(12) United States Patent
Petrus

(10) Patent No.: US 7,136,820 B1
(45) Date of Patent: Nov. 14, 2006

(54) METHOD/PROCESS OF DETERMINING A PERSONAL DIETARY SUPPLEMENT PROFILE AND RECOMMENDING DIETARY SUPPLEMENTS FOR AN INDIVIDUAL

(75) Inventor: Edward J. Petrus, Austin, TX (US)

(73) Assignee: Advanced Medical Instruments, Austin, TX (US)

( * ) Notice: Subject to any disclaimer, the term of this patent is extended or adjusted under 35 U.S.C. 154(b) by 462 days.

(21) Appl. No.: 09/444,660

(22) Filed: Nov. 22, 1999

(51) Int. Cl.
*G06F 19/00* (2006.01)

(52) U.S. Cl. .......................... 705/3; 434/262; 600/300
(58) Field of Classification Search .................. 705/2, 705/3
See application file for complete search history.

(56) References Cited

U.S. PATENT DOCUMENTS

| | | | |
|---|---|---|---|
| 4,464,122 A * | 8/1984 | Fuller et al. ................. 283/115 |
| 4,499,064 A * | 2/1985 | Shive ........................... 435/14 |
| 4,733,354 A | 3/1988 | Potter et al. | |
| 5,036,462 A | 7/1991 | Kaufman et al. | |
| 5,623,925 A | 4/1997 | Swenson et al. | |
| 5,692,501 A * | 12/1997 | Minturn ....................... 600/301 |
| 5,704,350 A | 1/1998 | Williams, III | |
| 5,937,387 A * | 8/1999 | Summerell et al. .......... 600/301 |
| 5,954,640 A * | 9/1999 | Szabo ........................... 600/300 |
| 5,976,568 A * | 11/1999 | Riley ........................... 424/451 |
| 6,210,686 B1 * | 4/2001 | Bell et al. .................... 424/400 |

FOREIGN PATENT DOCUMENTS

WO    WO 99/04043    *    1/1999

OTHER PUBLICATIONS

Troy, Mike; "New Attitudes Drive Product Sales," May 16, 1994, Drug Store News, pS6. (4 pages).*
Conlan MF, R.Ph's Lagging as Source for Supplement Information Drug Topics, Oct. 18, 1999 p. 58.

* cited by examiner

*Primary Examiner*—Joseph Thomas
*Assistant Examiner*—R. L. Porter

(57) ABSTRACT

This invention provides a method/process of determining a personal dietary supplement profile of vitamins, minerals, amino acids, enzymes, herbs, and other nutritional supplements for an individual based on information from a health questionnaire and comparing the individual's health information to an ideal health profile in a computer data base. Optionally, information provided by physical examination and laboratory studies can be incorporated into the method/process of determining the dietary supplement profile. The profile can be further defined by listing commercially available products that provide the suggested dietary supplements.

5 Claims, 2 Drawing Sheets

DIETARY SUPPLEMENT PROFILE

Name: John Consumer
Age: 60  DOB: 11/06/39  Sex: M
Weight: 200 lbs
Height: 5'11"
Date:

The following daily dietary supplements are recommended:

| | |
|---|---|
| Vitamin A (retinyl acetate) | 12,500 IU |
| Beta-Carotene | 10,000 IU |
| Vitamin $B_1$ (thiamine) | 30 mg. |
| Vitamin $B_2$ (riboflavin) | 30 mg |
| Vitamin $B_3$ (niacinamide) | 90 mg. |
| Vitamin $B_5$ (pantothenic acid) | 20 mg. |
| Vitamin $B_6$ (pyridoxal-5-phosphate) | 30 mg. |
| Vitamin $B_{12}$ (cyanocobalamine) | 200 mcg. |
| Biotin (d-biotin) | 300 mcg. |
| Choline (choline bitartrate) | 20 mg. |
| Folic acid | 800 mcg. |
| Vitamin C (ascorbic acid) | 300 mg |
| Vitamin D (cholecalciferol) | 100 IU |
| Vitamin E (d-α-tocopherol) | 200 IU |
| Vitamin K (phytonadione) | 60 mcg. |
| | |
| Boron (boron asparate) | 3 mg. |
| Calcium (calcium citrate) | 400 mg. |
| Chromium (chromium aspartate) | 20 mcg. |
| Copper (copper aspartate) | 250 mcg. |
| Iodine (kelp) | 150 mcg. |
| Iron | -0- |
| Magnesium (magnesium citrate) | 300 mg. |
| Manganese (manganese citrate) | 15 mg. |
| Molybdenum (molybdenum chelate) | 45 mcg. |
| Potassium (potassium citrate) | 90 mg. |
| Selenium (l-selenomethionine) | 150 mcg. |
| Vanadium (vanadium chelate) | 50 mcg. |
| Zinc (zinc citrate) | 30 mg. |

FIG. 2

METHOD/PROCESS OF DETERMINING A PERSONAL DIETARY SUPPLEMENT PROFILE AND RECOMMENDING DIETARY SUPPLEMENTS FOR AN INDIVIDUAL

FIELD OF THE INVENTION

A method and process for the selection of dietary supplements.

BACKGROUND OF THE INVENTION

We are all biochemically different, and our dietary nutrient requirements for optimal health vary. Each of us is unique due to variations in our genetics, lifestyle, dietary habits and health problems. If we were all the same, the same multivitamin-supplement with the same doses would provide the same results. Dr. Roger J. Williams, a pioneer in the field of nutrition and renowned biochemist, who discovered pantothenic acid (vitamin $B_5$), wrote extensively on "biochemical individuality" and has shown that every human is innately highly distinctive in terms of his biochemistry. Dr. Williams believed that no two individuals are identical in bodily structure and neither are their chemical processes always carried out in the same ways. Different persons need different combinations and amounts of food elements, vitamins and other nutrients.

Some 106 million Americans use vitamin and mineral supplements every day, and 45 million reported using herbal remedies regularly. Further, 74 million Americans are more likely to treat themselves than see or consult a physician. A recent survey noted that consumers have low confidence in labeling information and product safety, and that product labels, magazines, doctors, books and advertising all ranked ahead of pharmacists in providing information on dietary supplements. Lower than pharmacists as an information source, the survey noted, are health food stores and alternative medicine practitioners. One of the last places consumers used for information on dietary supplements was the Internet. Conlan M F, *Drug Topics*, Oct. 18, 1999, pg. 58.

Computerized programs for medical needs are not new to the art. Potter et al, U.S. Pat. No. 4,733,354 discloses an interactive method for performing a differential diagnosis using a programmed computer system and a stored data base. Kaufman et al, U.S. Pat. No. 5,036,462 discloses a medication delivery device. Swenson et al, U.S. Pat. No. 5,632,925 discloses a virtual medical instrument system for storing diagnostic test protocols. Williams III, U.S. Pat. No. 5,704,350 discloses a method for selecting foodstuffs to compare the user's daily dietary and physical activities to the user's recommended dietary allowance. None of the above cited patents teach or suggest the use of the method or process outlined in the present invention.

A more reliable source of information regarding the selection of dietary supplements is sought by consumers and provided by the present invention.

SUMMARY OF THE INVENTION

Because we are all biochemically different and our dietary supplement requirements will depend on lifestyle, dietary habits, health problems and current medications, a one-size fits all multivitamin supplement does not meet our individual needs. This invention offers the advantage of providing a personal dietary supplement profile and recommending dietary supplements based on information from a health history questionnaire, that can be further refined by incorporating physical exam findings and laboratory studies.

BRIEF DESCRIPTION OF THE DRAWINGS

FIG. 2 is a sample dietary supplement profile.

DETAILED DESCRIPTION OF THE INVENTION

Figure 1:
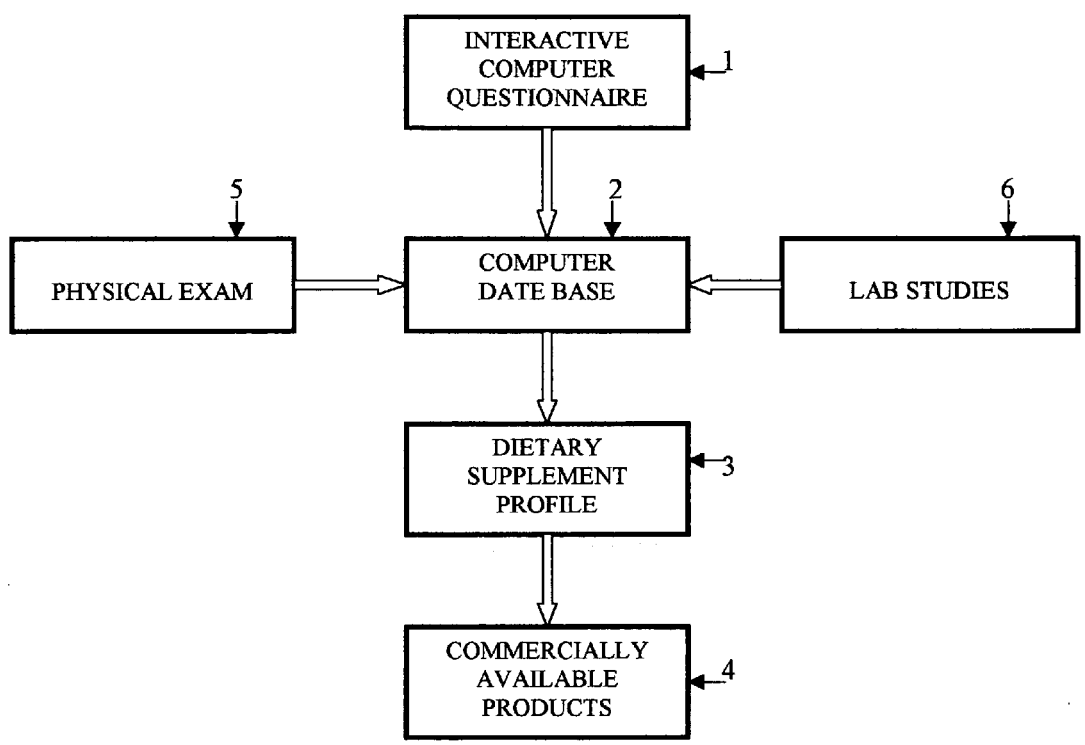
FIG. 1 is a diagram of the process for determining the dietary supplement profile for an individual.

With reference to FIG. 1, the principal components used to implement the present invention are illustrated in a block diagram. At the top of the diagram the consumer completes a health history questionnaire 1. The questionnaire can be in paper form to be entered into the computer database, or an interactive computer format that inquires about the family history, personal health history, environmental history, diet and meal pattern, food supplements, and symptom history. This information is entered and stored in the computer database 2, where it is compared to a health profile for a person of the consumer's age and health history background. Based on this comparison, a dietary supplement profile 3 can be generated that calculates the consumers personal nutritional needs of vitamins, minerals, amino acids, enzymes, herbs and other nutritional supplements to achieve optimal health and wellness. Optimal health is not the absence of disease but a positive state of mental and physical well-being. The dietary supplement profile 3 can be further defined into commercially available products 4, for both the convenience of the consumer or for the benefit of the commercial provider.

The health history questionnaire 1, may include a family history of parents, grandparents, siblings and children identifying the most consistent illness or health problems, if known, such as alcoholism, Alzheimer's disease, arthritis, diabetes, cancer, high blood pressure, liver disease, kidney disease, heart disease, gout, mental illness, obesity, congenital defects and any disease known to have a strong tendency to be inherited. Personal health history may inquire about childhood illnesses, serious accidents, illnesses, abnormal blood test results, surgeries, weight history, prescription and nonprescription medications, use of tobacco products, alcohol and illicit drugs, current major health problems, change in life situations, employment, work environment, allergies, and stress. A diet and meal pattern history and supplements currently used. A symptom history explores many health problems from insomnia, appetite, foods, bowel habits, skin problems, nail and hair problems, emotional complaints, fatigue, menstrual difficulties and stress.

The consumer's dietary supplement profile 3 can be further individualized by supplementing information provided by a physical exam 5 which allows the practitioner to input data such as blood pressure, pertinent physical and emotional findings, current medications, body fat analysis, and any contraindications to dietary supplements. Laboratory studies 6 can also be incorporated into the database 2, that provides additional insight into the consumers health status. Laboratory studies that could be input into the database by example comprise: complete blood count and urinalysis, automated blood analyses, serum vitamin levels, hair analyses or essential metabolic analysis for nutritional assessment testing.

The computer analysis can evaluate and compare the individual's health information with standardized profiles based on age, sex, physical activity, dietary habits, past medical history and other items covered in the questionnaire. Some dietary supplement considerations by example include the following: Persons with a high cholesterol or a family history of heart disease could increase vitamin E to 400 IU, vitamin C to 1 gm, beta-carotene to 25,000 IU, chromium to 200 mcg, magnesium to 400 mg; Persons over age 60 should increase zinc intake to 50 mg, calcium to 1.5 gm, vitamin E to 400 IU, beta-carotene to 25,000 IU, vitamin D to 800 IU, magnesium to 400 mg, chromium to 200 mcg and delete iron; If a woman is on a contraceptive pill to increase vitamin $B_6$ to 50 mg; If the woman is menopausal or postmenopausal increase calcium to 1.5 gm, magnesium to 400 mg, vitamin E to 400 IU and delete iron; If a smoker or in an air-polluted area increase vitamin C to 1 gm, selenium to 400 mcg, beta-carotene to 25,000 IU, vitamin E to 400 IU, copper to 3 mg and zinc to 50 mg; If the subject exercises three times a week increase vitamin E to 400 IU, magnesium to 400 mg, vitamin $B_1$ to 100 mg and zinc to 50 mg; If more than ten alcoholic beverages are consumed a week increase vitamin $B_1$ to 100 mg, folic acid to 800 mcg and vitamin C to 1 gm. If the subject is underweight or overweight a recommended weight management program can be provided with the profile.

The invention is further illustrated by the example shown in FIG. 2, which is to be regarded as illustrative only, and in no way limit the scope of the invention. In this example, a vitamin and mineral profile is presented for supplementation to the individual's current regimen. Amino acids, enzymes, herbs and other supplements can be incorporated into the profile. The profile can also show a comparison with past profiles to determine any changes in nutritional status. The profile can also be further defined in terms of commercial products available by companies who provide supplements for the public.

Although illustrative embodiments of the invention have been shown and described, a wide range of modifications, change, and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed is:

1. A method/process of creating a dietary supplement profile for an individual comprising:
    a) completing a health questionnaire by an individual,
    b) comparing of the questionnaire information by an individual to an optimal health profile in a computer data base,
    c) adjusting for differences in the individual's health information when compared to an optimal health profile,
    d) generating a computer-implemented dietary supplement profile based on the individual's health information listing the vitamins, minerals, amino acids, enzymes, and herbs suggested for an optimal health profile.

2. The method/process of creating a dietary supplement profile of claim 1, wherein step (b) comprises comparing the questionnaire information by the individual and information provided by a physical examination to a health profile in a computer database.

3. The method/process of creating a dietary supplement profile of claim 1, wherein step (b) comprises comparing the questionnaire information provided by the individual and information provided by laboratory studies to a health profile in a computer database.

4. The method/process of creating a dietary supplement profile of claim 1, further comprises adding a list of commercially available products that provide the dietary supplements listed in an optimal health profile.

5. The method/process of creating a dietary supplement profile of claim 1, further comprises adding a plan for weight management.

* * * * *